US00PP26084P3

(12) United States Plant Patent
Nixon et al.

(10) Patent No.: US PP26,084 P3
(45) Date of Patent: Nov. 17, 2015

(54) APRICOT TREE NAMED 'MAC12/54'

(50) Latin Name: *Prunus armeniaca*
Varietal Denomination: Mac12/54

(71) Applicant: The New Zealand Institute for Plant and Food Research Limited, Auckland (NZ)

(72) Inventors: Arlene E. Nixon, Alexandra (NZ); Michael T. Malone, Havelock North (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 190 days.

(21) Appl. No.: 13/987,024

(22) Filed: Jun. 26, 2013

(65) Prior Publication Data

US 2013/0347153 P1 Dec. 26, 2013

Related U.S. Application Data

(60) Provisional application No. 61/664,298, filed on Jun. 26, 2012.

(51) Int. Cl.
*A01H 5/08* (2006.01)

(52) U.S. Cl.
USPC ..... Plt./186
CPC ..... *A01H 5/0843* (2013.01)

(58) Field of Classification Search
USPC ..... Plt./186
See application file for complete search history.

*Primary Examiner* — Susan McCormick Ewoldt
(74) *Attorney, Agent, or Firm* — Lathrop & Gage LLP

(57) ABSTRACT

A new and distinct apricot variety is described. The variety results from selection among a population of seedlings derived from controlled crossing of the varieties 'Bhart' (not patented), marketed as Orangered™, and an unreleased selection (not patented) which was the result of crossing 'Cluthagold' (not patented) and 'Late Moorpark' (not patented). The new variety is distinguished from others by the late harvest date and rose/red overcolor of the mature fruit accompanied by mid orange colored firm flesh with high soluble solids content. Fruit of 'Mac12/54' matures in early to mid February in Otago, New Zealand.

4 Drawing Sheets

Genus and species of plant claimed: *Prunus armeniaca.*
Variety denomination: 'Mac12/54'.

BACKGROUND TO THE INVENTION

Seedlings obtained from the deliberate crossing of 'Bhart' (not patented) (female parent), marketed as Orangered™ and an unreleased selection (not patented) (male parent) resulting from crossing 'Cluthagold' (not patented) and 'Late Moorpark' (not patented), in September 2003, were planted out at Clyde, Otago, New Zealand, where the cross was also conducted. In February 2008, 'Mac12/54' was identified as having potential as a new variety. Later in 2008, 'Mac12/54' was asexually propagated from budwood taken at Clyde and budded at Hawkes Bay onto 'Golden Queen' (not patented) peach seedlings, the standard apricot rootstock in New Zealand. The resulting trees were planted out at Clyde in the Southern Hemisphere winter of 2009, and were subsequently found to be true to type demonstrating that the characteristics of the new variety, 'Mac12/54', are stable and transmitted without change through succeeding generations.

SUMMARY OF THE INVENTION

'Mac12/54' is characterised by medium sized fruit (80-100 g) with rose/red overcolor with mid orange colored firm flesh with high soluble solids content which mature in early to mid February in Otago, New Zealand. 'Mac12/54' is distinguished from a number of other varieties by the following characteristics:

'Mac12/54' is harvested one to two weeks later and has a stronger flavour when compared with fruit of 'Cluthagold' (not patented).

The fruit flesh of 'Mac 12/54' is finer in texture and deeper in color that of 'F194' (U.S. Plant Pat. No. 16,119) (also known as 'Southern Cross'), and the skin color is a deeper orange.

The fruit skin color of 'Mac12/54' is a deeper orange color with a higher sheen than that of 'F168' (U.S. Plant Pat. No. 16,071) (also known as 'Larclyd', marketed as Genevieve).

Mac12/54 differs from Mac12/45 (U.S Ser. No. 13/987,025) in that Mac12/54 is less precocious than Mac 12/45. Mac 12/54 also has more intense fruit flavour compared to its sibling Mac12/45.

Fruit of Mac12/54 is harvested approximately one month later than its parent 'Bhart'

Mac12/54 differs from its other parent, an unreleased seedling as Mac12/54 has an orange background fruit skin color while the unreleased seedling parent has a yellow/pale orange background fruit skin color.

BRIEF DESCRIPTION OF THE DRAWINGS

The accompanying photographs show typical specimens of the plant, fruit, and leaves of the new variety was depicted in colors as nearly true as is reasonably possible to make the same color in illustrations of this character.

DETAILED DESCRIPTION

Figure 1:
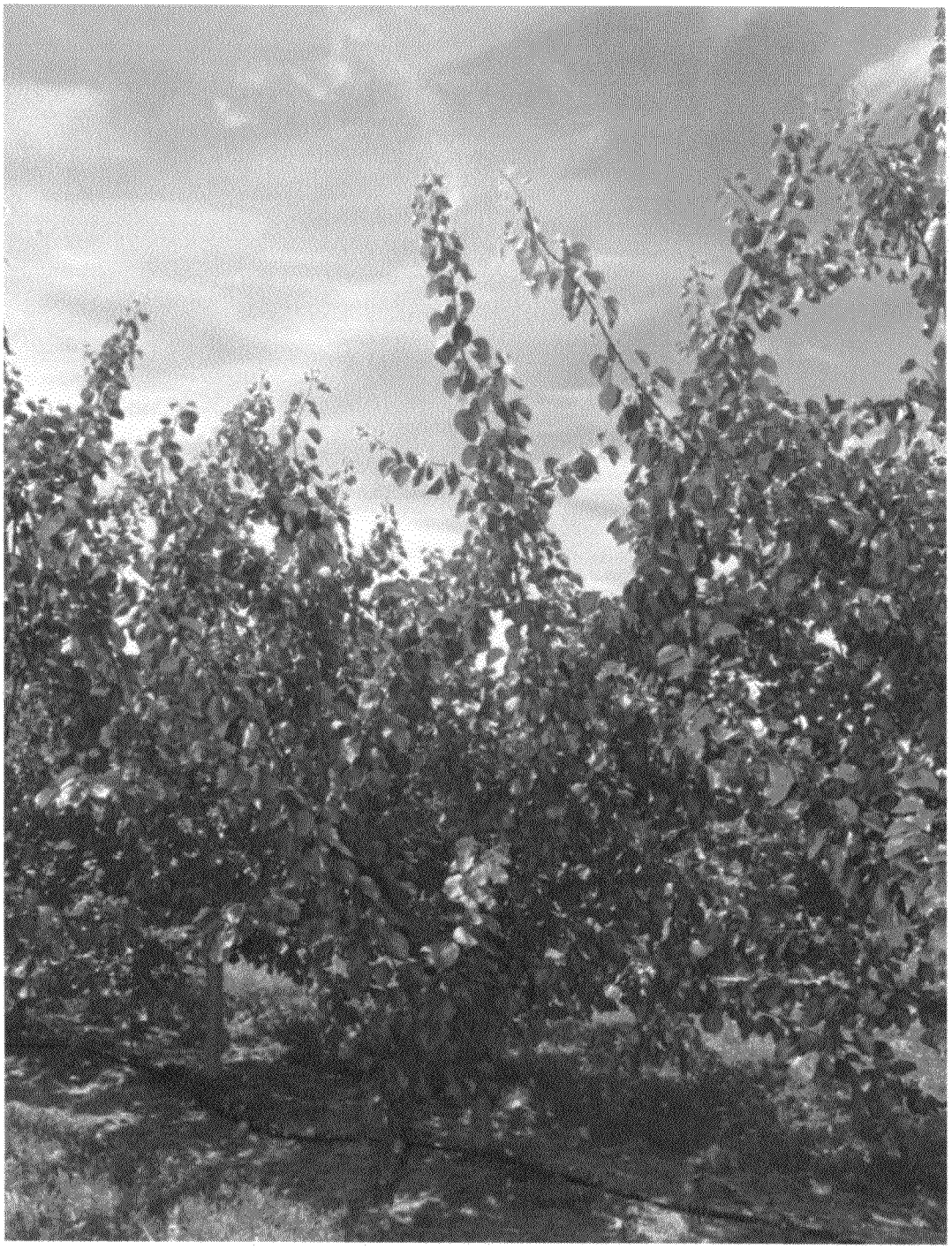
FIG. 1 shows a five year old 'Mac12/54' tree with fruit.
Figure 2:
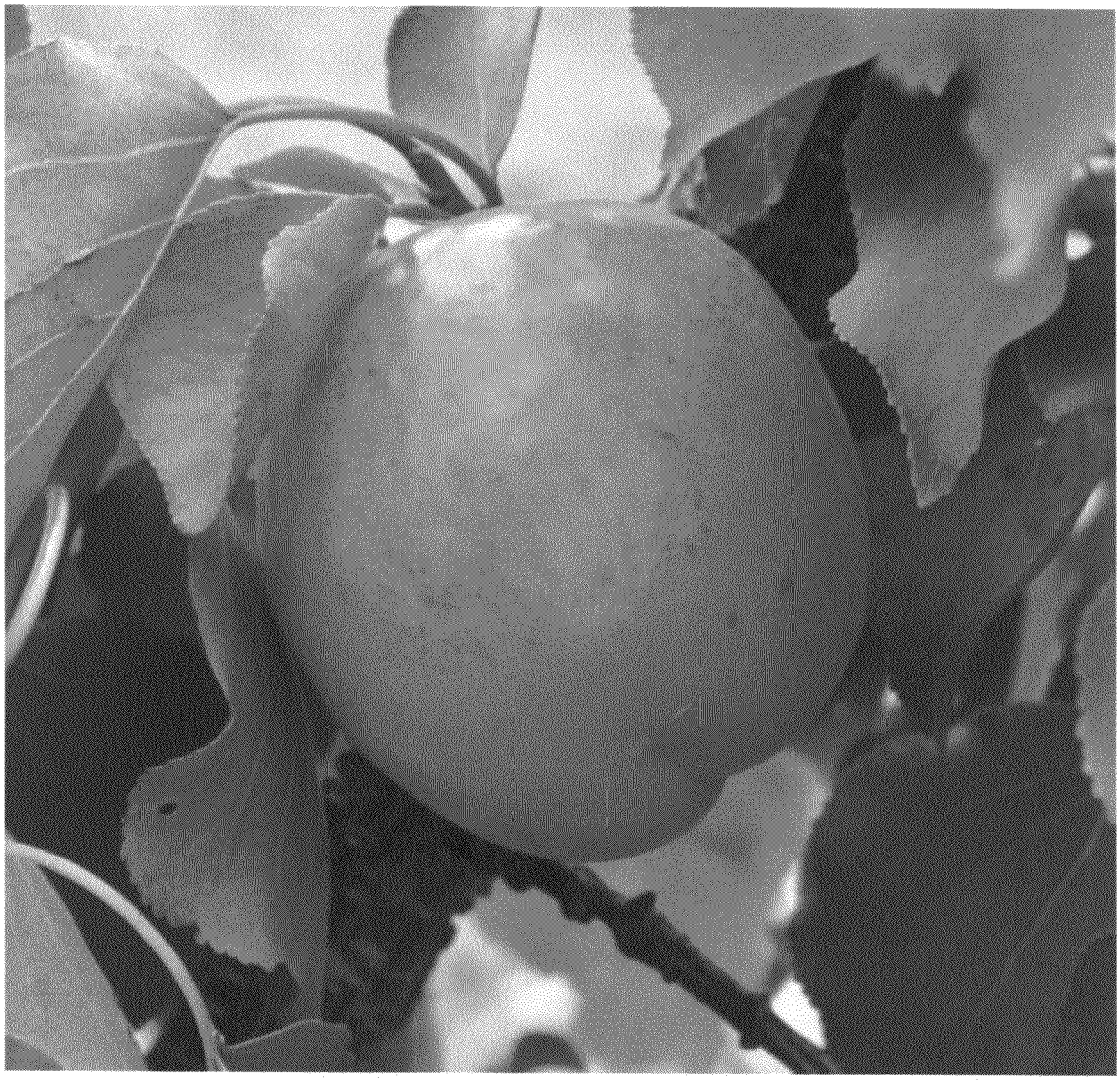
FIG. 2 shows a 'Mac12/54' fruit on the tree.
Figure 3:
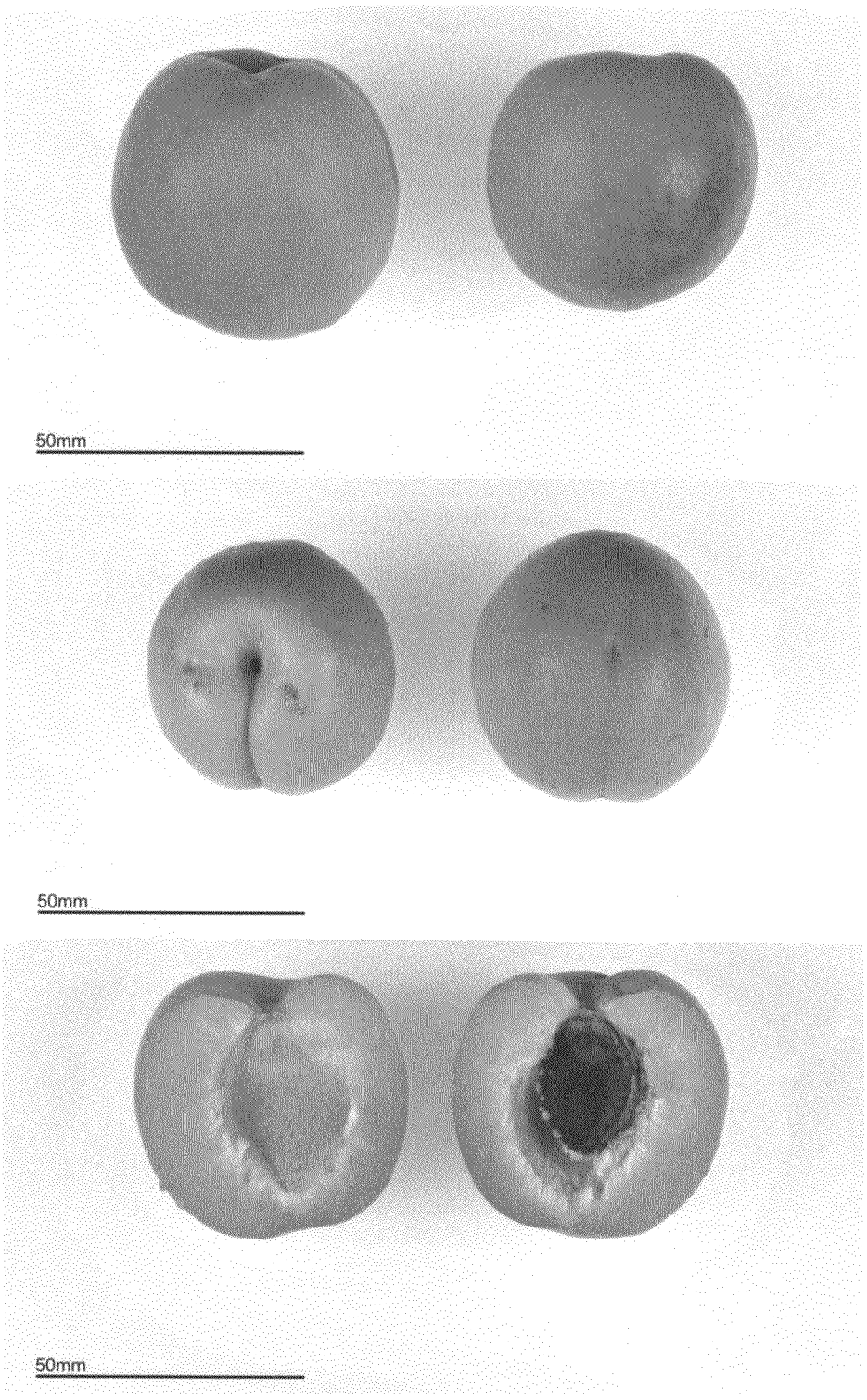
FIG. 3 shows whole and cut 'Mac12/54' fruit.
Figure 4:
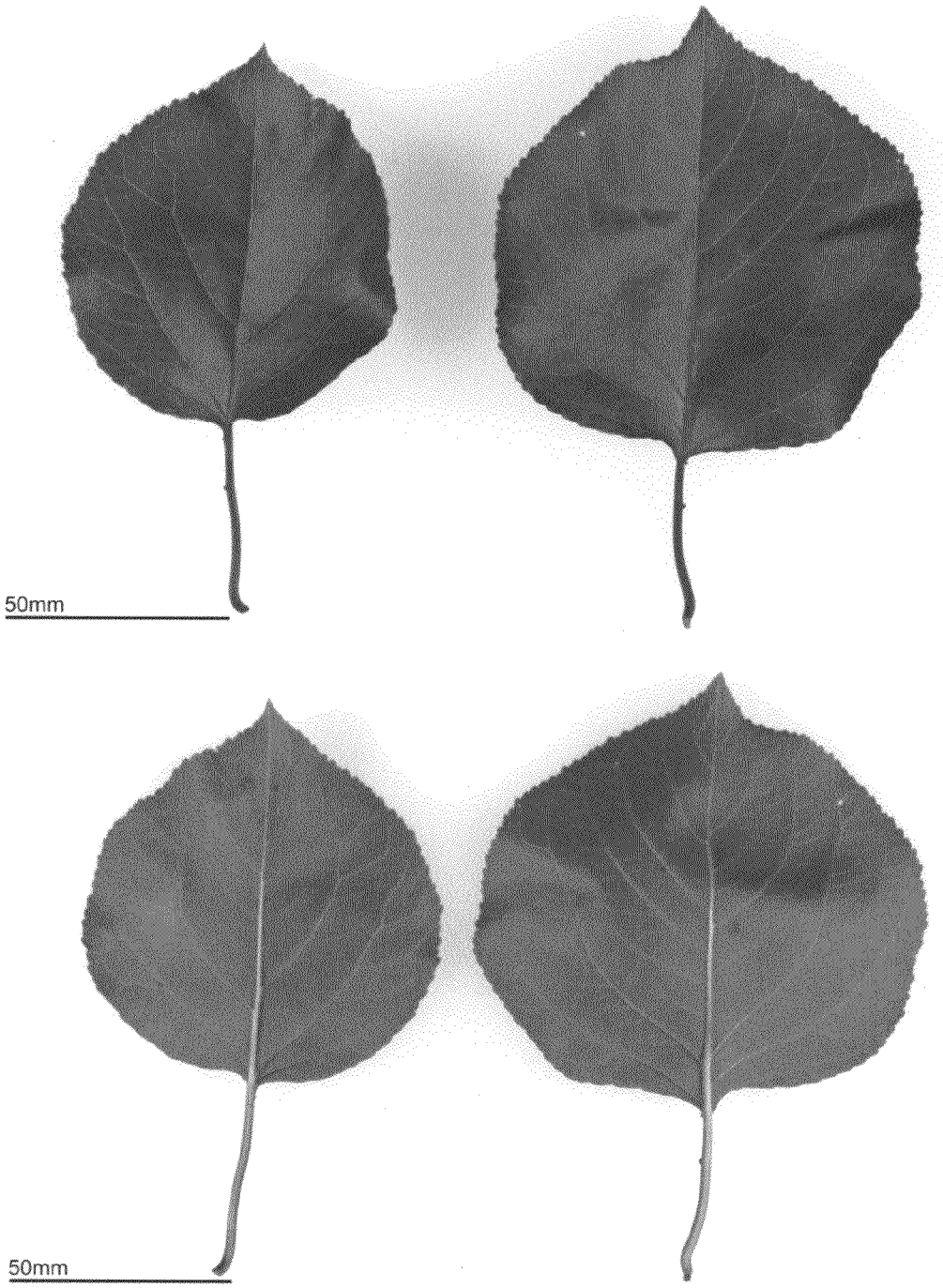
FIG. 4 shows upper and underside of 'Mac12/54' leaves.

The following is a brief description of the new variety with color terminology in accordance with The Royal Horticultural Society Colour Charts (R.H.S.C.C.) 2001 edition. The specimens described were grown at Clyde, New Zealand. The observations were made of the 2012-2013 seasons on 5 year old mature trees.

Tree: Average of approximately 3.0 m tall with a spread of approximately 2.0 m, medium vigour with an upright to spreading habit. 'Mac12/54' scions are compatible on peach seedlings ('Golden Queen') rootstocks. Tree health is considered to be good under Central Otago conditions in New Zealand.

Trunk: Average circumference of a mature trunk, approximately 30 cm from the graft union, is 285 mm. Trunk color was observed to be near brown N200B, with reticulate bark texture, and a sparse-medium density distribution of near greyed yellow 161D oblanceolate lenticels which averaged approximately 3.0 mm long and 2.0 mm wide.

One-year-old shoot: Observed in winter were observed to be near greyed orange 166A in color with near greyed orange 166A, medium sized bud supports which averaged approximately 4.7 mm in diameter and 3.3 mm in height. Dormant buds were observed to be ovate, moderately elongated, near brown 200A in color and approximately 3.4 mm long and 2.0 mm wide.

Leaves: The leaves examined were fully expanded and harvested from the central third of growing shoots in summer. The overall shape of the leaves was observed to be broadly ovate with a moderately obtuse acuminate tip approximately 7.9 mm long, a truncate base and crenate margins with a medium undulation, and moderately concave profile in cross section. Leaves are arranged alternatively and averaged 85.8 mm long and 80.3 mm wide. The color of the upperside was a medium intensity matte near green 137A, and the color of the underside was near green 137C. The venation pattern of the leaf was reticulate and the color of the venation was near yellow green 145D.

Petiole: The average petiole length of fully expanded leaves was 31.8 mm and 1.9 mm in diameter. The upperside of the petioles had a medium anthocyanin coloration of near red purple 59B and an underside coloration of near red purple 60A. Petioles were observed to have between two and three medium sized nectaries close to the leaf base which had an average diameter of 1.2 mm.

Flowers: Observations were made at full bloom unless otherwise stated. Timing of beginning of flowering, 10% flowers open, was recorded in early September (approximately 7$^{th}$ September), with full bloom, 90% of flowers open, occurring mid September (approximately 13$^{th}$ September). The average diameter of a an open flower with petals pressed flat was 27.0 mm and borne equally on spurs and one-year old shoots, flowers had a medium intensity fragrance.

Corolla: Five petals per flower, with an average length of 11.1 mm (excluding claw) and an average width of 9.6 mm and a 1.2 mm claw. The petal shape (excluding claw) was approximately circular with a smooth but sinuate margin. Petals were near white, N155D, at full bloom.

Stamens: An average of 26 per flower. Filaments were translucent white in color, and an average of 7.1 mm long, with near yellow orange 17C anthers and near greyed yellow 162A pollen. Anthers were on average 1 mm long and 0.9 mm wide.

Carpel: Pistals were on average 8.1 mm and the stigma sat at approximately the same level relative to the anthers.

Calyx: Five sepals per flower, average length of 6.1 mm and width of 3.3 mm with an acute apex and smooth margin. Colored near red purple 64A.

Pedicel: Average approximately 5.4 mm long and 3.4 mm wide.

Fruit: Fruit at horticultural maturity were large in size and observed to be on average 99 g, with an average height of 56.9 mm, average lateral width of 58 mm, and an average ventral width of 55.4 mm. 'Mac12/54' fruit were symmetric and were circular in lateral and ventral view with a slightly sunken suture and a retuse apex. The stalk cavity depth was medium, approximately 6.6 mm. The skin surface was smooth with minimal pubescence, weak gloss, a background color of near orange 25B and N25B, and approximately 5% overcolor colored near orange red N34A made up of isolated spots. The flesh color was near orange 25B and near orange 25B in the stone cavity with no whiteness around the stone. The flesh texture was fine with medium firmness, an average of 2.8 kgf, with a weak adherence to the stone and average soluble solids of approximately 18.5%.

Stone: Observations were made on dry stones unless otherwise stated. Stones were circular in shape, lateral view, with an obtuse apex, and obtuse base. Stones were on average approximately 32 mm long, with an average lateral width of 28 mm and colored near greyed orange 165B.

Harvest timing: Fruit begin ripening late in the season, approximately 8$^{th}$ February in Clyde New Zealand.

Use: Fresh eating.

Pest and disease: 'Mac12/54' has no known particular tolerances or susceptibilities to pests and diseases associated with apricot trees.

The invention claimed is:

1. A new and distinct apricot plant substantially as herein illustrated and described.

* * * * *